US010004853B2

(12) United States Patent
Lin Lee et al.

(10) Patent No.: US 10,004,853 B2
(45) Date of Patent: Jun. 26, 2018

(54) PREFILLABLE AUTO-RETRACTABLE SAFETY SYRINGE

(71) Applicant: BENCHA INTERNATIONAL GROUP INC., Tortola (VG)

(72) Inventors: Lee Lin Lee, Taipei (TW); Wen-Hsu Chang, Taipei (TW)

(73) Assignee: BENCHA INTERNATIONAL GROUP INC., Tortola (VG)

( * ) Notice: Subject to any disclaimer, the term of this patent is extended or adjusted under 35 U.S.C. 154(b) by 898 days.

(21) Appl. No.: 14/081,456

(22) Filed: Nov. 15, 2013

(65) Prior Publication Data

US 2014/0180216 A1   Jun. 26, 2014

Related U.S. Application Data

(60) Provisional application No. 61/740,207, filed on Dec. 20, 2012.

(51) Int. Cl.
*A61M 5/32* (2006.01)
*A61M 5/315* (2006.01)

(52) U.S. Cl.
CPC .......... *A61M 5/3221* (2013.01); *A61M 5/315* (2013.01); *A61M 5/31511* (2013.01); *A61M 5/322* (2013.01); *A61M 5/3232* (2013.01); *A61M 2005/31518* (2013.01)

(58) Field of Classification Search
CPC .............. A61M 5/315; A61M 5/31511; A61M 5/3221; A61M 5/322; A61M 5/3232; A61M 5/3278; A61M 2005/31515; A61M 5/34; A61M 5/323; A61M 5/31516
See application file for complete search history.

(56) References Cited

U.S. PATENT DOCUMENTS

| 4,994,045 A | * | 2/1991 | Ranford | ............... | A61M 5/3271 604/198 |
| 7,674,241 B2 | | 3/2010 | Lin Lee | | |
| 8,088,110 B2 | | 1/2012 | Lin Lee et al. | | |
| 8,449,505 B2 | | 5/2013 | Lin Lee | | |

(Continued)

FOREIGN PATENT DOCUMENTS

| CN | 102711877 A | 10/2012 |
| JP | 2013-517072 A | 5/2013 |

(Continued)

*Primary Examiner* — Laura Bouchelle
(74) *Attorney, Agent, or Firm* — Muncy, Geissler, Olds & Lowe, P.C.

(57) ABSTRACT

A retractable safety syringe includes a retractable needle hub holding a needle and having a first guiding means; and a hollow barrel having a second guiding means set correspondingly to the first guiding means; and a collapsible plunger comprising of a first plunger element having a protrusion releasably coupled with a second plunger element having a longitudinal slot with a pinched zone to curb the movement of said protrusion; and a spring disposed between the needle hub and hollow barrel and acts between the needle hub and the hollow barrel. The uncoupling of the collapsible plunger triggers the retraction mechanism to enable the needle hub to retract into the barrel by the decompression force of a spring. The reliability of retraction is further improved by a longitudinal slot and a protrusion to facilitate the retreating of the collapsible plunger in an orderly way.

17 Claims, 19 Drawing Sheets

(56) References Cited

U.S. PATENT DOCUMENTS

| | | | | |
|---|---|---|---|---|
| 2003/0187401 A1* | 10/2003 | Doyle | ............... | A61M 5/3243 |
| | | | | 604/198 |
| 2004/0181190 A1* | 9/2004 | Hsu | ............... | A61M 5/322 |
| | | | | 604/240 |
| 2007/0219492 A1* | 9/2007 | Lucas | ............... | A61M 5/322 |
| | | | | 604/110 |
| 2008/0021389 A1* | 1/2008 | Runfola | ............... | A61M 5/3234 |
| | | | | 604/110 |
| 2009/0216154 A1 | 8/2009 | Lin Lee | | |
| 2009/0259195 A1 | 10/2009 | Lin Lee | | |
| 2009/0318880 A1* | 12/2009 | Janish | ............... | A61M 5/31511 |
| | | | | 604/228 |
| 2013/0085452 A1* | 4/2013 | Schiff | ............... | A61M 5/31511 |
| | | | | 604/218 |

FOREIGN PATENT DOCUMENTS

| | | |
|---|---|---|
| TW | M400327 U1 | 3/2011 |
| WO | WO 2009/127077 A1 | 10/2009 |
| WO | WO 2009/127077 A1 | 7/2011 |

* cited by examiner

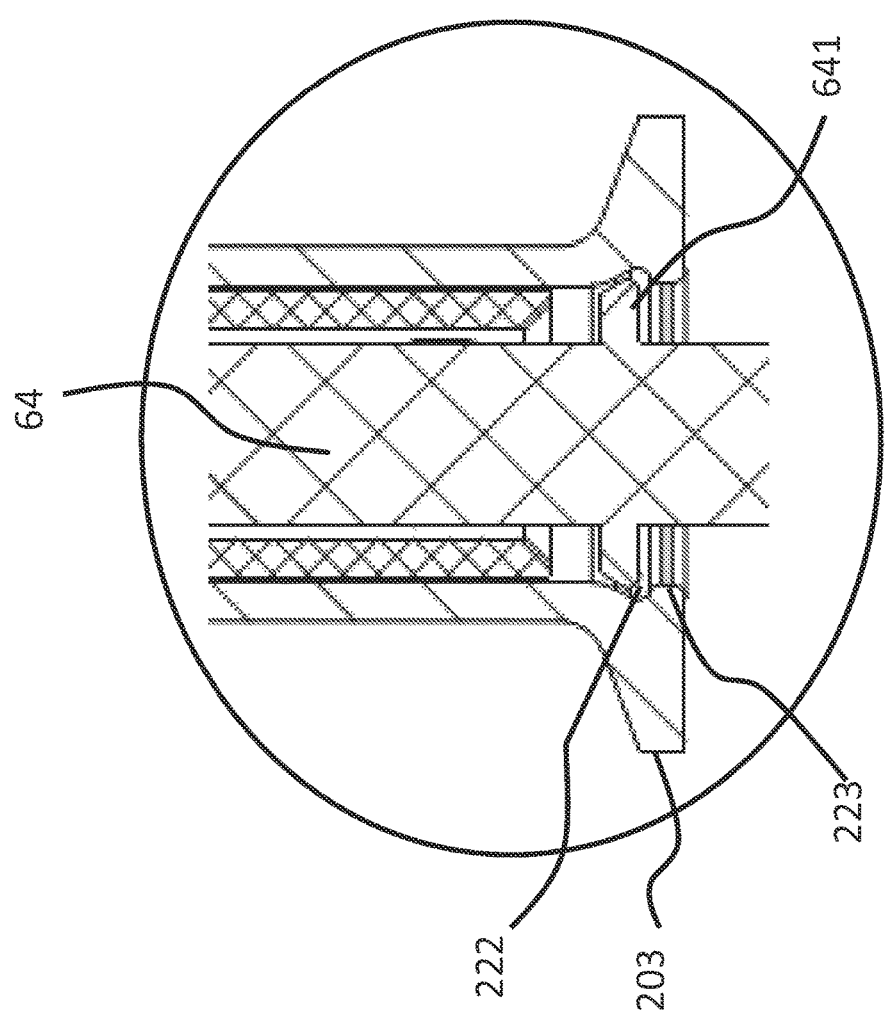

PREFILLABLE AUTO-RETRACTABLE
SAFETY SYRINGE

CROSS-REFERENCE TO RELATED
APPLICATIONS

This application claims the benefit of priority under 35 U.S.C. § 119(e) to U.S. provisional application No. 61/740,207 filed Dec. 20, 2012. The aforementioned provisional application is incorporated herein by reference in its entirety.

BACKGROUND OF THE INVENTION

1. Technical Field

The present invention relates to a retractable safety syringe and, more particularly, to a prefillable auto-retractable safety syringe including a retractable needle assembly and a collapsible plunger operable to facilitate the retraction of needle after the injection is completed.

2. Description of Related Art

Bloodborne diseases such as AIDS, hepatitis A, or hepatitis C, are transmitted through contact with blood or body substances. Bloodborne pathogens are known for transmitting serious or fatal diseases, and that the major transmitting route is an accidental needle-stick injury caused by inadvertent operation of a syringe, or inappropriate reuse of needles. An improper operation or disposal of syringes with exposed needles often leads to accidental needle-stick injury, and healthcare workers are thus easily exposed to bloodborne pathogens, and even hospital employees may be exposed to significant risk of contagion. Moreover, reusing an unsterilized or contaminated syringe may result in the spread of diseases, Unfortunately, reusing or sharing needles is significant among drug addicts, and unauthorized use of a syringe is commonly associated with a use of illegal drugs, that dramatically increases the risk of infection, and the consequent spread of those bloodborne diseases becomes a serious threat to public health.

In order to reduce the mentioned risks and the problems, non-reusable safety injection devices or syringes are nowadays widely used. Currently, safety syringes using a spring-based mechanism are the most common design for automatically retracting the needle after injecting. For example, U.S. Pat. No. 8,088,110 B2 entitled "AUTOMATICALLY RETRACTABLE SAFETY INJECTION DEVICE FOR NON-LIQUID MATERIAL" disclosed a safety syringe.

As shown in FIGS. 1A and 1B, a conventionally known safety syringe 9 has a cap 900, a needle hub 91 connecting a needle 90, a hollow barrel 92 connecting the needle hub 91, an annular spring 93 in a compressed state, and a collapsible plunger combination 94 settled in the hollow barrel 92. The collapsible plunger combination 94 includes a rod 941 with a plunger head 942, a retractable plunger 95 and a hollow plunger 96. The hollow barrel 92 is disposed with a plurality of elastic and slightly flexible retaining hook 922 at the front end thereof, while the needle hub 91 is formed with a plurality of slots 913, slopes 914, turning chutes 915 and guiding chutes 916. The retaining hooks 922 of the hollow barrel 92 engage with the slots 913 to clamp the needle hub 91 during the operation the safety syringe 9 until the injection of an injectant 97 is completed. The retaining hooks 922 start to be indirectly pressed and flexibly expanded to be disengaged with the slots 913 when the user continuously presses the hollow plunger 96 after the injection of the injectant 97 is completed, and the retaining hooks 922 consequently slides along the slopes 914, the turning chutes 915, and the guiding chutes 916 in an order to decompress the annular spring 93 so as to guide and push the needle hub 91 backward into the hollow barrel 92.

Regarding the disclosed syringe 9, it is noted that the disengagement of the retaining hooks 922 of the hollow barrel 92 with the slots enables the annular spring 93 not only to be decompressed but also to be rotated, and this rotation of the annular spring 93 is likely to impede the retraction of the needle hub 91 and therefore the needle hub 91 would not be completely retracted into the hollow barrel as good as desired or even fails to start the retraction. As a result, the whole retraction mechanism still has malfunction possibilities and become less reliable, and therefore causes the user to be under the mentioned threat.

However, these safety syringes by their nature have sophisticated design, increased number of parts, and consequently requires complicated fabrication procedures, which often leads to lower product yield rate and higher production costs. The higher cost of safety syringes, apart from the concern of functional reliability, is a major obstacle of marketing the advanced safety syringes.

Therefore, aiming at providing flawless protection against needle-stick injuries to healthcare workers to prevent from infection of potentially fatal bloodborne pathogens, an improved and safer design for a safety syringe is provided hereinafter.

BRIEF SUMMARY OF THE INVENTION

A primary objective of this invention is to provide an automatic retractable safety syringe capable of performing a user-activated needle retraction that can be conveniently operated and are less likely to fail to complete the retraction due to an improper operation during an injection process.

Another objective of this invention is to provide an automatic retractable safety syringe capable of performing a user-activated retraction that are less likely to be damaged during assembling process of manufacturing so as to have higher quality, reliability and yield, thus waste of raw materials and the costs of processing are reduced.

A further objective of this invention is to provide an automatic retractable safety syringe capable of performing an user-activated retraction that can be easily made by plastic injection molding, the neat configurations render molds tooling easier and the molded components have more consistent dimensions, so that the rejected components due to dimensional variation is substantially reduced.

Yet another objective of this invention is to provide an automatic retractable safety syringe capable of performing a user-activated retraction wherein a collapsible plunger has a predetermined mechanical strength, so that a needle can be automatically retracted when a force exceeding said mechanical strength is applied to break up the collapsible plunger and trigger off the retraction mechanism instantly.

Based on the aforesaid objectives, this invention provides an automatic retractable safety syringe capable of performing an user-activated retraction for various kinds of injection including intramuscular injection, hypodermic injection, and intravenous injection, wherein the retractable safety syringe and the collapsible plunger allows for only single use.

A retractable safety syringe is proposed herein and the retractable safety syringe includes those elements and the interrelations as well as the functions thereof in the following description.

The retractable safety syringe according to the invention includes a needle hub having a first end to receive and hold a needle extending distally, a nearby first guiding means on an external (Rem: Use internal vs. external) wall of the needle hub, and a second end being opposite to the first end.

The retractable safety syringe according to the invention includes a hollow barrel having an internal surface defining a chamber allowing the needle hub releasably disposed in the chamber of the hollow barrel, a distal open end allowing the first end of the needle hub to protrude distally, and having a second guiding means nearby on a sidewall of the hollow barrel, and a proximal open end being opposite to the distal open end.

The retractable safety syringe according to the invention includes a collapsible plunger slideably fitted into the hollow barrel, having a first plunger element having a proximal end and a distal end, a second plunger element being releasably coupled with the first plunger element, wherein the first plunger element is formed with a protrusion near the distal end of the first plunger element, and the second plunger element has a longitudinal slot on a sidewall of the second plunger element to accommodate the protrusion of the first plunger element allowing the protrusion to slide longitudinally along the longitudinal slot, and the longitudinal slot has a proximal part formed with a pinched zone to curb the protrusion and a distal part, so that the first and the second plunger elements are coupled until the pinched zone deforms to disengage the protrusion from the pinched zone, allowing the protrusion sliding toward the distal part of the longitudinal slot, so that the first and the second plunger elements become axially slideable with respect to each other.

The retractable safety syringe according to the invention includes a spring disposed between the needle hub and the internal surface of the hollow barrel such that the spring acts between the needle hub and the hollow barrel.

The needle hub of the aforesaid retractable safety syringe is further formed with at least a fluid path extending longitudinally through the needle, to be in fluid communication with the chamber.

The first guiding means of the aforesaid retractable safety syringe releasably engages with a first portion of the second guiding means, so that the first and the second guiding means are capable of releasably holding the needle hub against an expansion force of the spring until the first guiding means disengage from the first portion of the second guiding means and moves toward a second part of the second guiding means to initiate retraction of the needle hub.

According to the aforesaid retractable safety syringe, the first guiding means is a protrusion, and the second guiding means is a curved track formed on the internal surface of the hollow barrel and configured to receive the first guiding means. The second guiding means extends along a direction being at an angle preferably from 45 degrees to 75 degrees measured from a horizontal plane defined when the whole retractable syringe is situated vertically with the needle orientated upward. More preferably, the angle is 60 degrees measured from the horizontal plane.

According to the aforesaid retractable safety syringe, the collapsible plunger is capable of enduring a force less than 98N, so that in normal use the first and the second plunger elements will not be uncoupled. Preferably, the first plunger element is a rod or a cylinder; and the second plunger element is a sleeve or a hollow cylinder.

According to the aforesaid retractable safety syringe, the second plunger element further has a plurality of apertures being adjacent to the pinched zone.

According to the aforesaid retractable safety syringe, the first plunger element is provided with a locking means having one or one more annular raised portions near the proximal end, the one or one more annular raised portions being received and snap-locked by an annular recessed portion and an adjacent annular raised portion inside the flange of the hollow barrel, such that the first plunger element is constrained with the hollow barrel by the locking means when the first plunger element is fully pressed into the hollow barrel.

According to the aforesaid retractable safety syringe, the needle hub further has a lumen at the second end for receiving a plug having an elongated cylinder portion protruding into the lumen and a disc portion, wherein a sealing element is further provided and shaped for being adapted to the needle hub; and the sealing element is disposed between the second end of the needle hub and the disc portion of the plug.

According to the aforesaid retractable safety syringe, the fluid path is an internal channel extending longitudinally throughout the plug. The fluid path is composed of a plurality of longitudinal recesses alongside an external surface of the elongated cylinder portion of the plug.

BRIEF DESCRIPTION OF THE SEVERAL VIEWS OF THE DRAWINGS

The invention as well as preferred modes of use, and advantages thereof will be best understood by referring to the following detailed description of illustrative embodiments in conjunction with the accompanying drawings, wherein:

FIG. 5 is an enlarged view of either section C or section C' of the retractable safety syringe and the collapsible plunger thereof according to the first and the second embodiment of the invention shown in FIG. 3C and FIG. 4E.

DETAILED DESCRIPTION OF THE INVENTION

Hereinafter, a detailed description of this invention will be provided below with reference to embodiments thereof. Other advantages and features of this invention will be readily appreciated by those skilled in the art upon reviewing this disclosure. However, this invention may also be implemented or applied as other embodiments, and various details in this specification may be modified and altered from different viewpoints and based on different applications without departing from the spirit of this invention.

To better understand the spatial arrangement among the individual elements of the retractable safety syringe, as well as the relative motions or interrelation therein, hereinafter a distal end (portion) of an element means the end (portion) facing toward the needle; and a proximal end (portion) of the element means the end (portion) opposite to the distal end (portion) which facing toward the thumb rest of the plunger being operated.

Figure 1A:
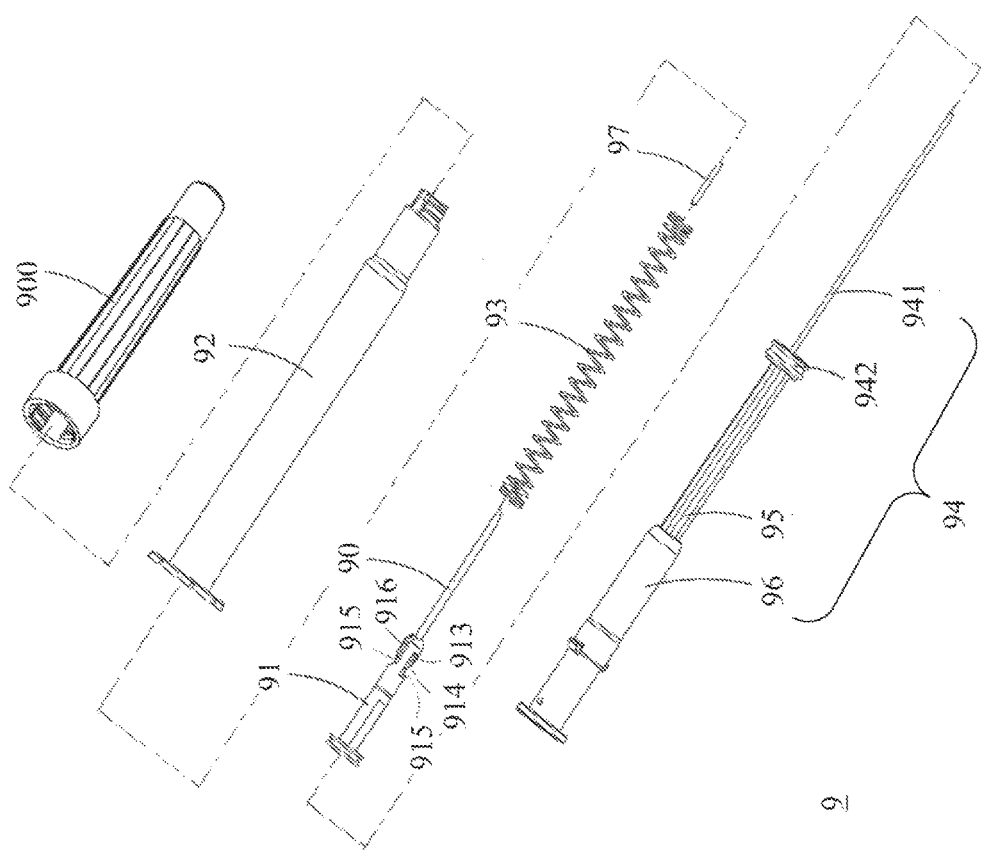
FIG. 1A is an exploded perspective view of a conventionally known safety syringe.
Figure 1B:
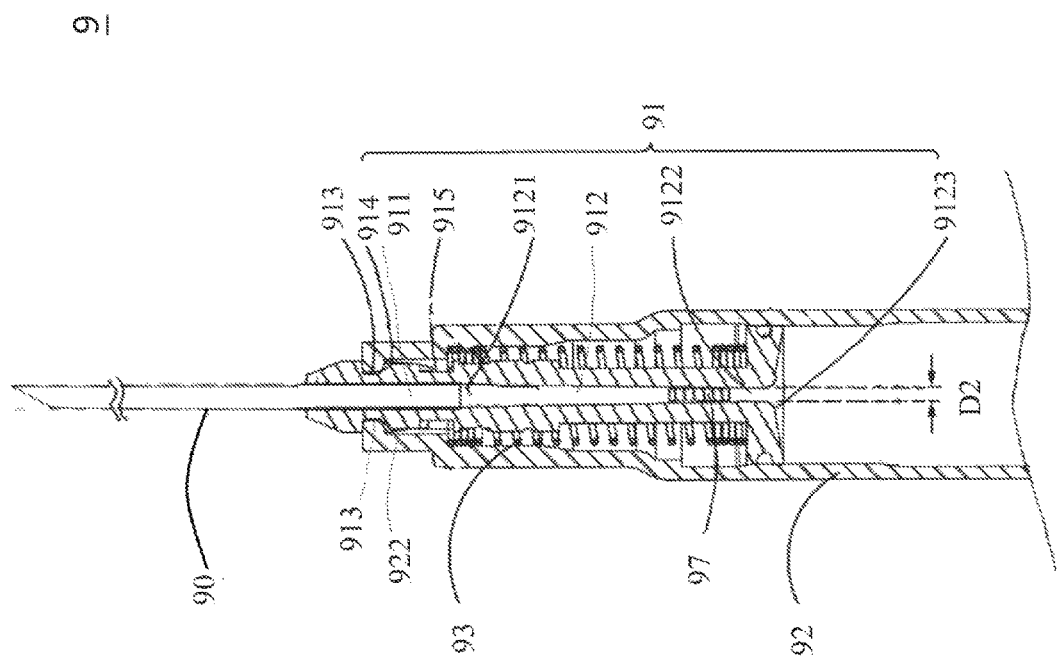
FIG. 1B is a cross-sectional view of the conventional known safety syringe showing mainly the needle hub and the hollow barrel of the safety syringe.
Figure 2A:
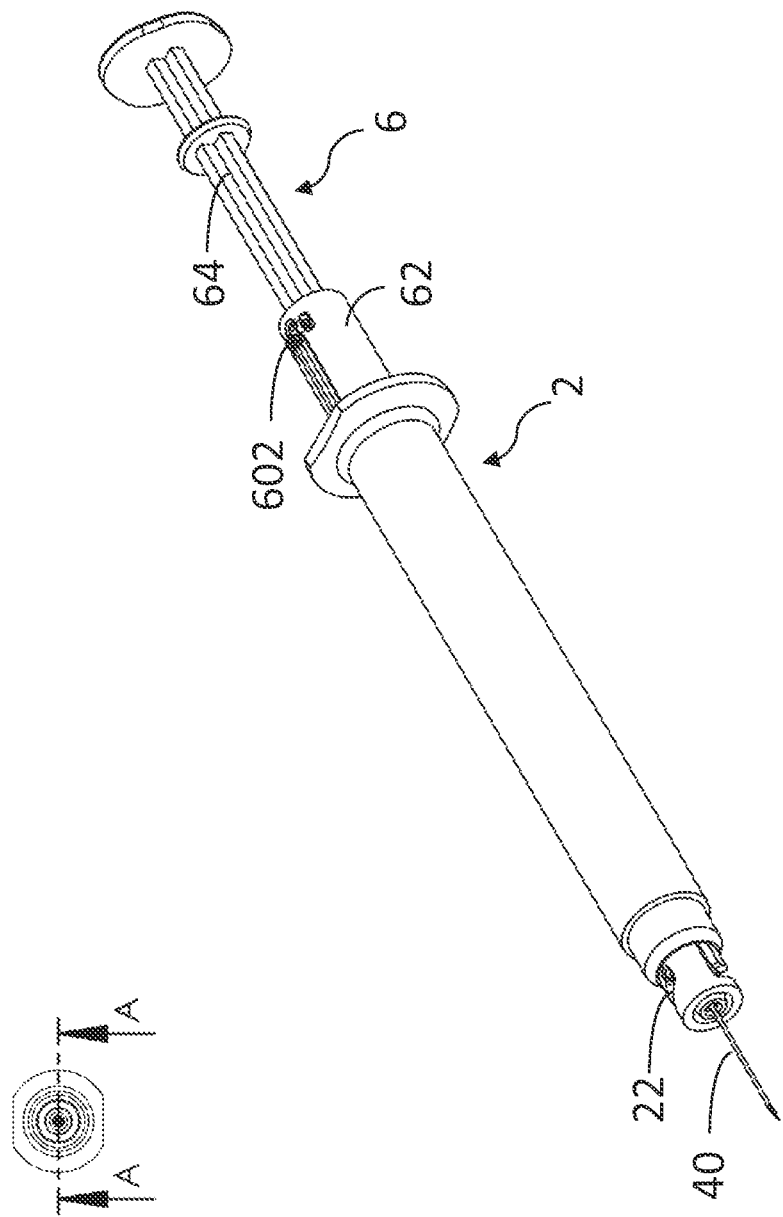
FIG. 2A is a perspective view of a retractable safety syringe and a collapsible plunger thereof showing that the needle hub and the collapsible plunger are not yet inserted into the hollow barrel according to a first embodiment of the invention.
Figure 2B:
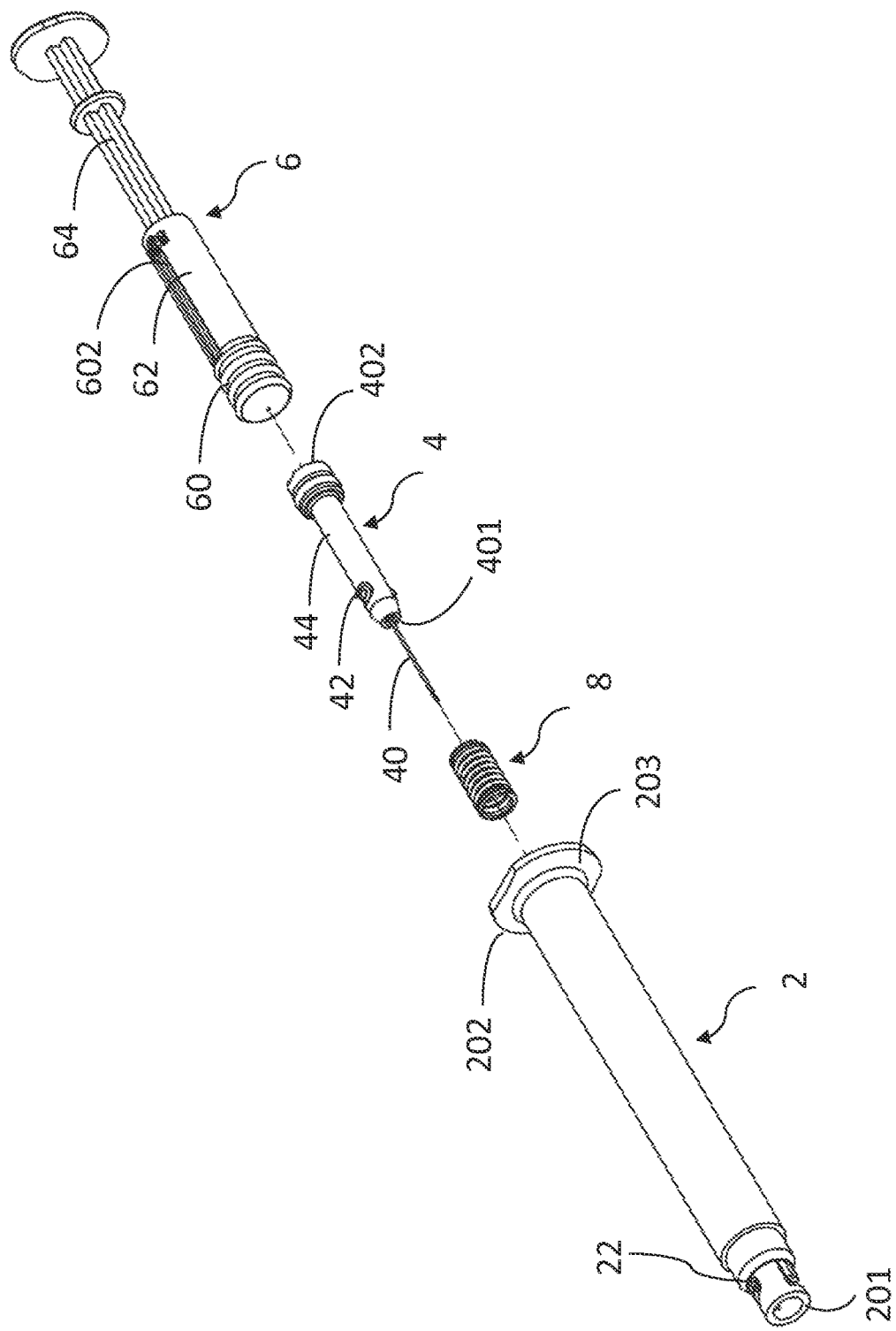
FIG. 2B is an exploded perspective view of the retractable safety syringe and the collapsible plunger thereof according to the first embodiment of the invention.

Referring to FIGS. 2A and 2B, a retractable safety syringe 1 according to a first embodiment of this invention includes the needle 40, needle hub 4, hollow barrel 2, spring 8, and collapsible plunger 6 which are as described in the following contents.

A retractable needle hub 4 has a first end 401 which is a distal end and a second end 402 which is a proximal end. An opening is formed at the distal end 401 to receive and hold a needle 40 extending distally; and a nearby first guiding means such as a protrusion 42 is formed on an external side wall 44 of the needle hub 4. The proximal end 402 is opposite to the distal end 401.

A hollow barrel 2 has a distal open end 201 and a proximal open end 202 which is opposite to the distal open end 201. The distal open end 201 is formed with an opening to allow the needle 40 to protrude outward the hollow barrel 2 or to retract inward the hollow barrel 2; and a second guiding means such as a curved track 22 is formed nearby on a side wall of the hollow barrel 2. The proximal open end 202 of the hollow barrel 2 is formed with a flange 203 and an opening. The hollow barrel 2 has an internal surface 21 defining a chamber 20 allowing the needle hub 4 releasably disposed in the chamber 20 of the hollow barrel 2.

A compressible spring 8 is interposed between the external sidewall 44 of the needle hub 4 and an internal sidewall of the hollow barrel 2; and the decompression of the spring 8 will drive the needle hub 4 moving into the hollow barrel 2.

A collapsible plunger 6 slideably fits into the hollow barrel 2. The collapsible plunger 6 has a first plunger element such as a plunger rod 64 formed with a protrusion 603 (shown in FIG. 2H) near its distal end, and a second plunger element such as a plunger sleeve 62 with a longitudinal slot 602 being formed on its side wall, wherein the plunger sleeve 62 is releasably coupled with the plunger rod 64; and preferably the plunger rod 64 is partially telescoped into and releasably interlocked with the plunger sleeve 62 by lodging the protrusion 603 inside the longitudinal slot 602.

Practically, when the retractable syringe 1 is used for an injection, the protrusion 603 of the plunger rod 64 is curbed at a pinched zone 6021 (shown in FIG. 2H) of the longitudinal slot 602 of the plunger sleeve 62. Referring to the FIG. 2H, the longitudinal slot 602 is configured to accommodate the protrusion 603 and has a pinched zone 6021 near the proximal end. The pinched zone 6021 is shaped to curb the movement of the protrusion 603 so that in normal use the collapsible plunger 6 will not be uncoupled. In other words, the plunger rod 64 is immobilized due the constraint of the pinched zone 6021 until the pinched zone 6021 is yielded to an excess external force. Practically, the collapsible plunger 6 is preferably capable of enduring a force less than 98N, so that in normal use, the plunger rod 64 and the plunger sleeve 62 will not be uncoupled.

A plurality of apertures 604 may be further formed to be adjacent to the pinched zone 6021 to render the plunger sleeve 62 relatively flexible or even frangible nearby the pinched zone 6021, and thus to facilitate the releasing of the curbed protrusion 603 once the excess force is applied. Once the protrusion 603 is forced to squeeze across the pinched zone 6021, thus to overcome the curb, the collapsible plunger 6 is uncoupled which allows the protrusion 603 to slide along the longitudinal slot 602, so that the plunger rod 64 and the plunger sleeve 62 become axially moveable relative to each other. When the plunger rod 64 and the plunger sleeve 62 collapse, the force exerting by the collapsible plunger 6 against the needle hub 4 is released, thus the retraction mechanism is activated, and the needle hub 4 is driven into the hollow barrel 2 by the expansion force of the spring 8, and the plunger sleeve 62 retreats consequently to encompass the plunger rod 64 via the sliding motions of the protrusion 603 along the longitudinal slot 602. On the other hand, the frangibility of the plunger sleeve 62 caused by devising the apertures 604 would render the collapsible plunger 6 un-reusable to avoid attempts to reuse the retractable safety syringe 1.

Figure 2C:
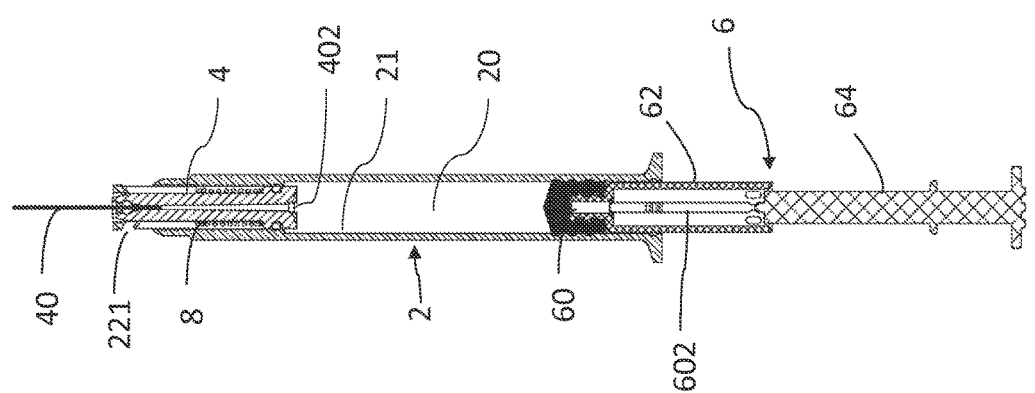
FIG. 2C is a cross-sectional view of the retractable safety syringe and the collapsible plunger thereof showing that the needle hub and the collapsible plunger are not yet inserted into the hollow barrel according to the first embodiment of the invention.
Figure 2D:
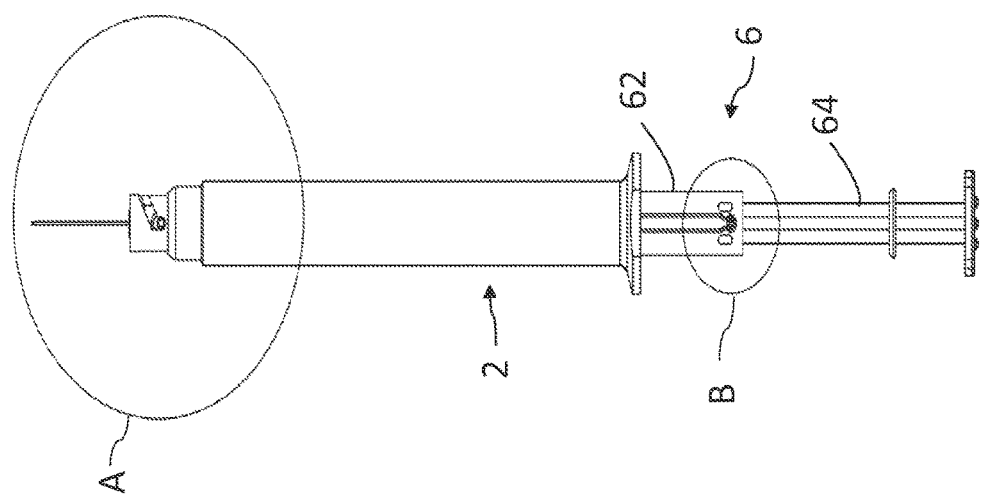
FIG. 2D is a front view of the retractable safety syringe and the collapsible plunger thereof showing that the needle hub and the collapsible plunger are not yet inserted into the hollow barrel according to the first embodiment of the invention.

Referring to FIGS. 2C and 2D, a cross-sectional view and a front view of the retractable safety syringe 1 and the collapsible plunger 6 thereof prior to an operation of injection are respectively shown, in which the retractable needle hub 4 and the collapsible plunger 6 are partially telescoped and not yet fully inserted into the hollow barrel 2 according to the first embodiment of the invention. In view of the assembly of the retractable safety syringe 1, the needle hub 4 is inserted into the hollow barrel 2 through the opening at the proximal open end 202 (shown in FIG. 2B) of the hollow barrel 2, and then the needle 40 is allowed to protrude the opening at the distal open end 201 (shown in FIG. 2B) of the hollow barrel 2. Once the needle hub 4 holding the needle 40 is properly inserted into the hollow barrel 2 and settled nearby the distal open end 201 of the hollow barrel 2, the needle hub 4 is accommodated inside the hollow barrel 2 through the coordination of the protrusion 42 (shown in FIG. 2B) of the needle hub 4 and the curved track 22 (shown in FIG. 2B) of the hollow barrel 2. Particularly, the protrusion 42 of the needle hub 4 is retained and guided by the curved track 22 of the hollow barrel 2, and the needle hub 4 is capable of sliding along the curved track 22.

The collapsible plunger 6 is inserted into the hollow barrel 2 through the opening at the proximal end 202 of the hollow barrel 2, indicating that the collapsible plunger 6 is partially telescoped into the hollow barrel 2 and is capable of moving back and forth inside the hollow barrel 2. Furthermore, a stopper 60 is provided to be mounted on the distal end of collapsible plunger 6. Thus, the collapsible plunger 6 can be pushed inside the hollow barrel 2 with the stopper 60 being contacted against the proximal end 402 of the needle hub 4.

Figure 2E:
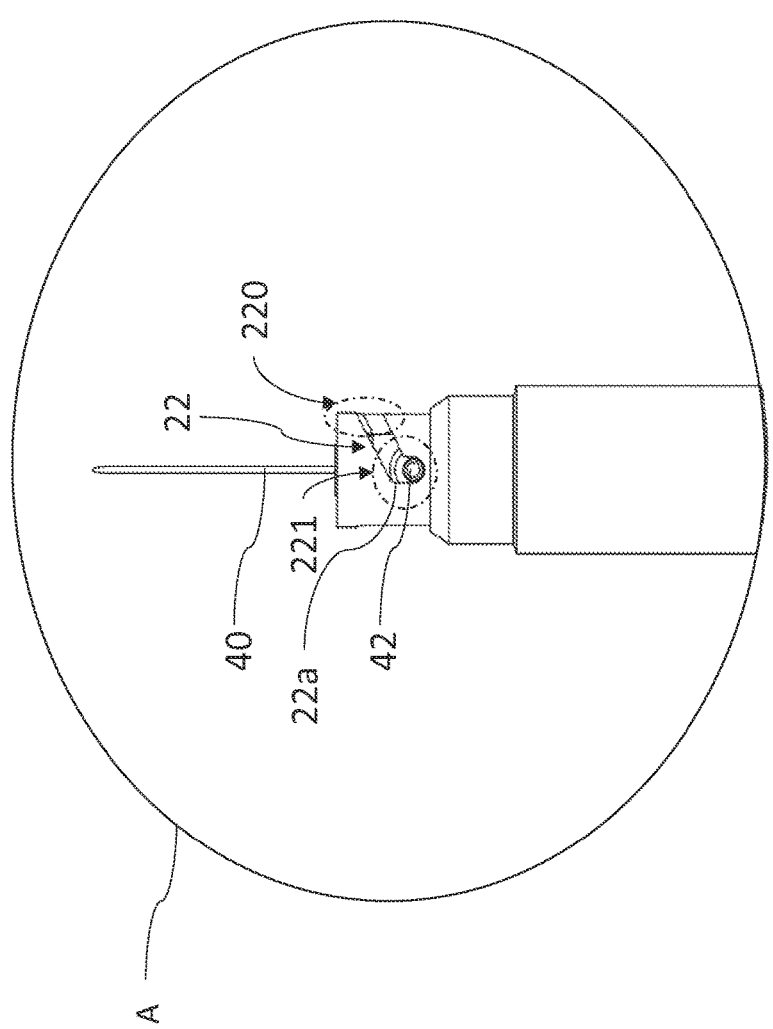
FIG. 2E is an enlarged view of a section A of the retractable safety syringe and the collapsible plunger thereof according to the first embodiment of the invention shown in FIG. 2D.

FIG. 2D shows a front view of the retractable safety syringe 1 and FIG. 2E further shows the enlarged view of a section A of the retractable safety syringe Referring to the section A of the retractable safety syringe 1 of the first embodiment of the present invention, the curved track 22 is designed to guide the protrusion 42 of the needle hub 4 to move in a sliding manner along the path of curved track 22, and thus the curved track 22 enables the needle hub 4 to rotate axially when the protrusion 42 is allowed to slide in the curved track 22. A horizontal plane is defined herein for better understanding of the technical features concerning the retraction mechanism of the retractable safety syringe 1. Specifically, the horizontal plane is defined as a plane perpendicular to the direction of the gravity; in other words, when the whole retractable syringe 1 is situated vertically with the needle orientated upward, the horizontal plane is defined as the plane passing transversely and horizontally (i.e., perpendicular to the direction of the gravity) through the retractable syringe 1, dividing the retractable syringe 1 into upper and lower parts.

Regarding the novel design of section A shown in FIG. 2E, the curved track 22 partially surrounds the hollow barrel 2 and enables the protrusion 42 to slide toward the distal end 201 (shown in FIG. 2B) or the proximal end 202 (shown in FIG. 2B) of the hollow barrel 2. Furthermore, the curved track 22 includes an first portion which is an anchoring portion 221 around the first curved site 22a (shown in FIG. 2E) of the curved track 22, and the anchoring portion 221 is utilized for a temporary engagement of the protrusion 42 with the curved track 22 so as to anchor the protrusion 42 as well as the needle hub 4 before the retraction mechanism is activated. Once a sufficient external pushing force is applied on the protrusion 42 to dislodge the protrusion 42 from the anchoring portion 221, and the protrusion 42 is forced to slide along the path of the curved track 22; and the protrusion 42 would be released and freed from the constraint of the aforementioned engagement, allowing the needle hub 4 to move toward the distal end 201 of the hollow barrel 2. In other words, the retraction mechanism is being activated. Moreover, the external pushing force not only drives the protrusion 42 to dislodge from the anchoring portion 221, but also contributes to the further sliding along the curved track 22, and thus the curved track 22 orientates the axial rotation as well as the movement of the needle hub 4 to a position ready for retraction, and the needle hub 4 would be subsequently retracted into the hollow barrel 2.

Figure 2F:
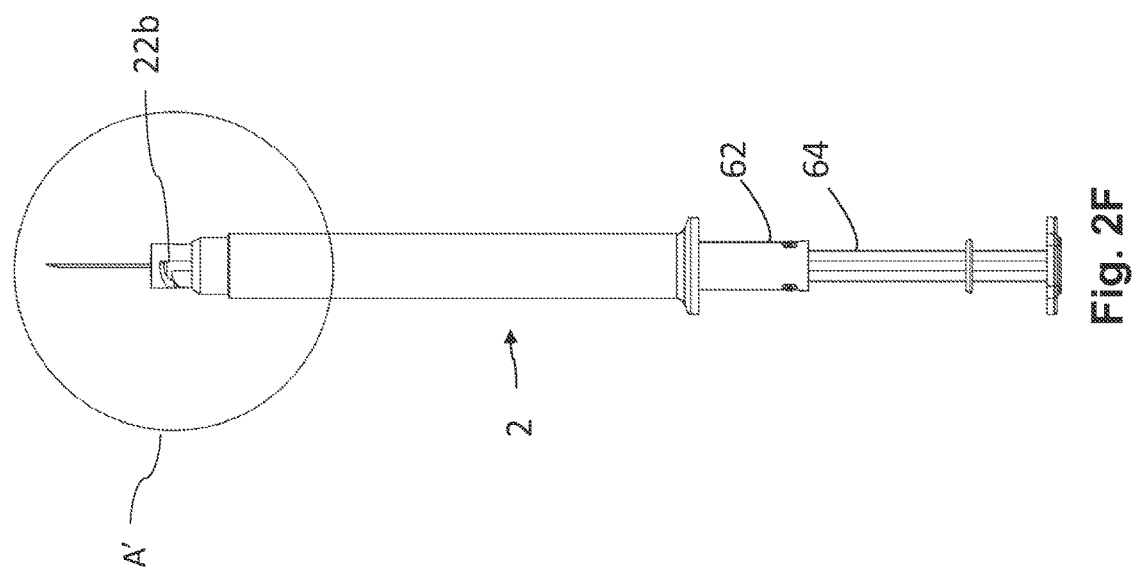
FIG. 2F is a side view of the retractable safety syringe and the collapsible plunger thereof showing that the needle hub and the collapsible plunger are not yet inserted into the hollow barrel according to the first embodiment of the invention.
Figure 2G:
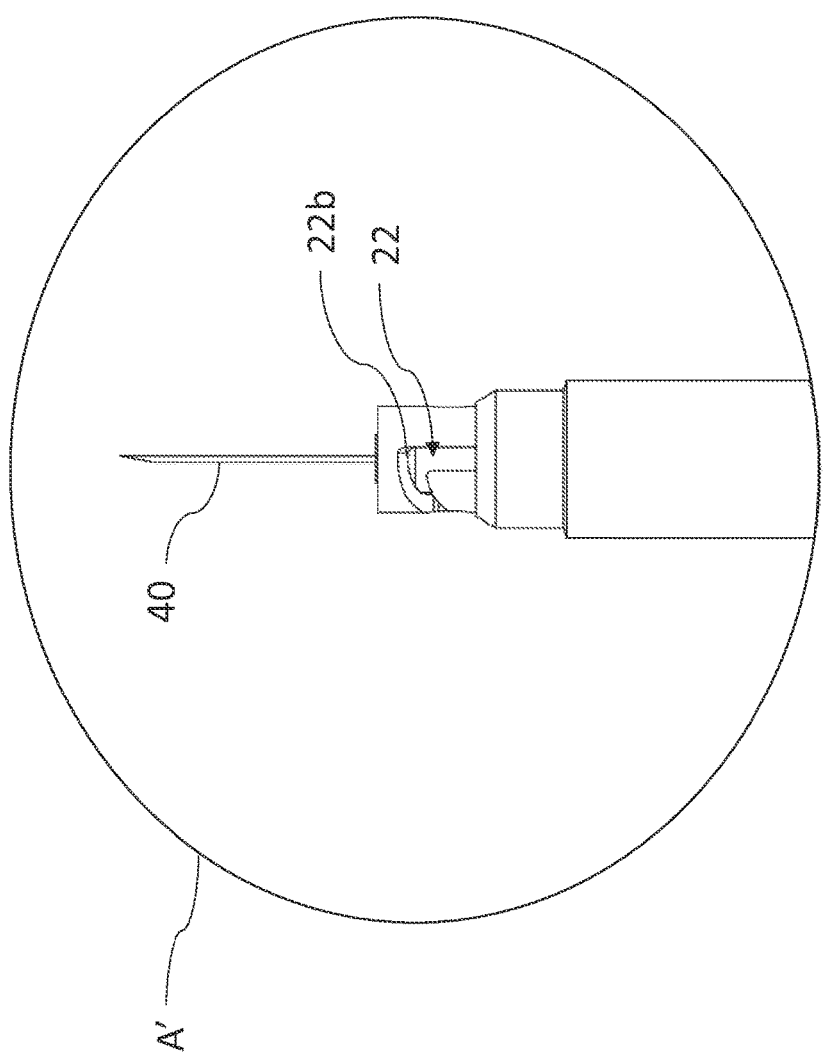
FIG. 2G is an enlarged view of a section A' of the retractable safety syringe and the collapsible plunger thereof according to the first embodiment of the invention shown in FIG. 2F.

Referring to FIG. 2F, showing a side view of the retractable safety syringe 1 and FIG. 2G shows an enlarged view of a section A' of the retractable safety syringe 1, prior to an operation of injection according to the first embodiment of the invention. Both FIGS. 2F and 2G show that the side view of the curved track 22 of the hollow barrel 2 and a second curved site 22b (shown in FIG. 2F, 2G). Particularly, the second curved site 22b is clearly shown to guide the protrusion 42 to veer and then move toward the proximal end 202 (shown in FIG. 2B) of the hollow barrel 2. Those skilled persons in the art can easily understand that, as long as the curve track 22 is optimized in curving angles and the corresponding length of the curved track 22, sufficient sliding force would be provided to trigger the protrusion 42 to turn and move toward the proximal end 202 of the hollow barrel 2, and at the same time, the snapback of the protrusion 42 initiates the decompression of the spring 8 (shown in FIG. 2B), which is coiled and compressed around the needle hub 4 until the aforementioned sliding force is transmitted to decompress the spring 8. Preferably, the curved track 22 has a part extending from the first curved site 22a along a direction being at an angle from 45 degrees to 75 degrees measured from the horizontal plane when the whole retractable safety syringe 1 is situated vertically with the needle orientated upward. More preferably the angle is 60 degrees measured from the horizontal plane.

The aforementioned modes of angle not only optimize the sliding of the protrusion 42 in the curved track 22 but also the rotation of the needle hub 4 toward the proximal end 202 of the hollow barrel 2, and results in the following initiation of the extraction mechanism of the needle hub 4. On the other hand, as soon as the extraction mechanism is activated, the collapsible plunger 6 is uncoupled to trigger the whole retraction mechanism.

Specifically, the expansion force derived from the spring 8 pushing the needle hub 4 moving into the barrel 2. In short words, the curved track 22 guides not only the forward movement (toward the distal end 201) the rotation of the needle hub 4 but also orientates the decompression force of spring 8 to facilitate the full retraction of needle hub 4 into the barrel 2.

Hence, it is an advantage of the present invention that the novel design for executing the retraction mechanism of the retractable safety syringe 1 provides a more reliable retraction mechanism significantly, and eliminates or at least significantly reduces the possibility of impediment on the spring action which often impedes the retraction of needle hub present in the conventional arts. Regarding the practical use of the retractable safety syringe 1 represented in the present invention, the reliability is significantly improved.

Figure 2H:
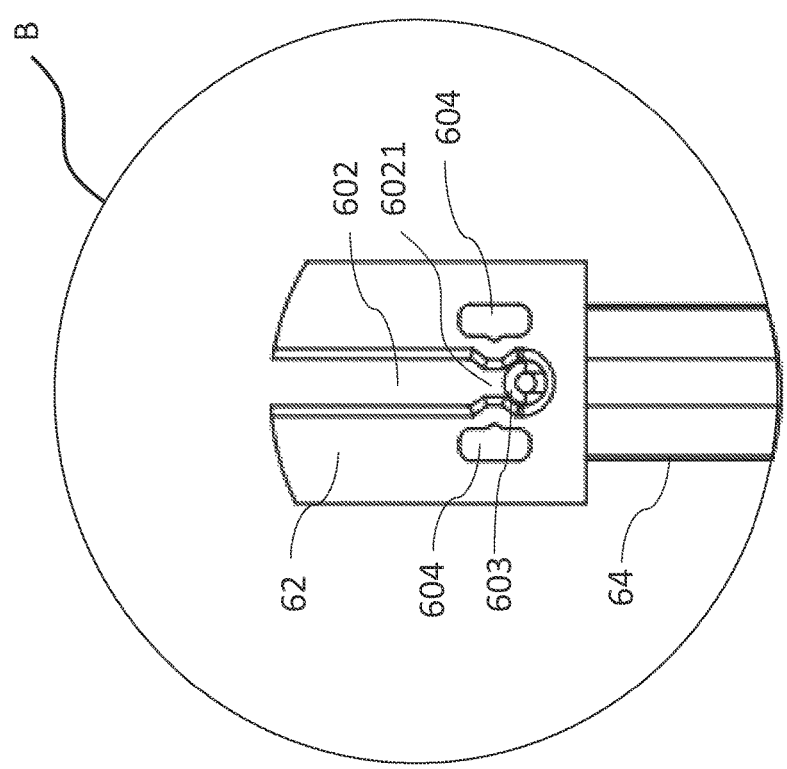
FIG. 2H is an enlarged view of a section B of the retractable safety syringe and the collapsible-plunger thereof according to the first embodiment of the invention shown in FIG. 2D.

Referring to FIG. 2H, showing an enlarged view of a section B of the collapsible plunger 6 of retractable safety syringe 1 according to the first embodiment of the invention shown in FIG. 2D. In order to properly initiate the retraction mechanism following completion of an injection, and more importantly, to prevent needle hub 4 from being accidentally or prematurely released from the distal end 201 (shown in FIG. 2B) of the hollow barrel 2 and being retracted into hollow barrel 2, the present invention provides further a solution by providing a plunger sleeve 62 having a plurality of apertures 604 that are adjacent to the pinched zone 6021 of the longitudinal slot 602 of the plunger sleeve 62. Practically, the plurality of apertures 604 are designed to render the portion of the plunger sleeve 62 nearby the pinched zone 6021 deformable, frangible or flexible to facilitate the releasing of the protrusion 603 from the curb at the pinched zone 6021. To be more specific, the collapsible plunger 6 is in contact with the needle hub 4 upon completion of an injection, when further pressed, the needle hub 4 will be dislodged from the anchoring portion 221 (around the first curved site 22a) and move forward; and the needle hub 4 will rotate till it reaches a foremost position (around the second curved site 22b) to be ready for the retraction, and when further pushing the plunger 6 to force the protrusion 603 to overcome the curb set by the pinched zone 6021, the collapsible plunger 6 is thus uncoupled so that the force exerting against the needle hub 4 by the collapsible plunger 6 is released, and the retraction mechanism is thus fully activated, meanwhile the expansion force of the spring 8 keeps driving the needle hub 4 moving into the hollow barrel 2; and at the same time, the plunger sleeve 62 retreats subsequently to encompass the plunger rod 64. Thus, a full retraction mechanism is facilitated by the coordination of the protrusion 603 and the longitudinal slot 602.

Figure 3A:
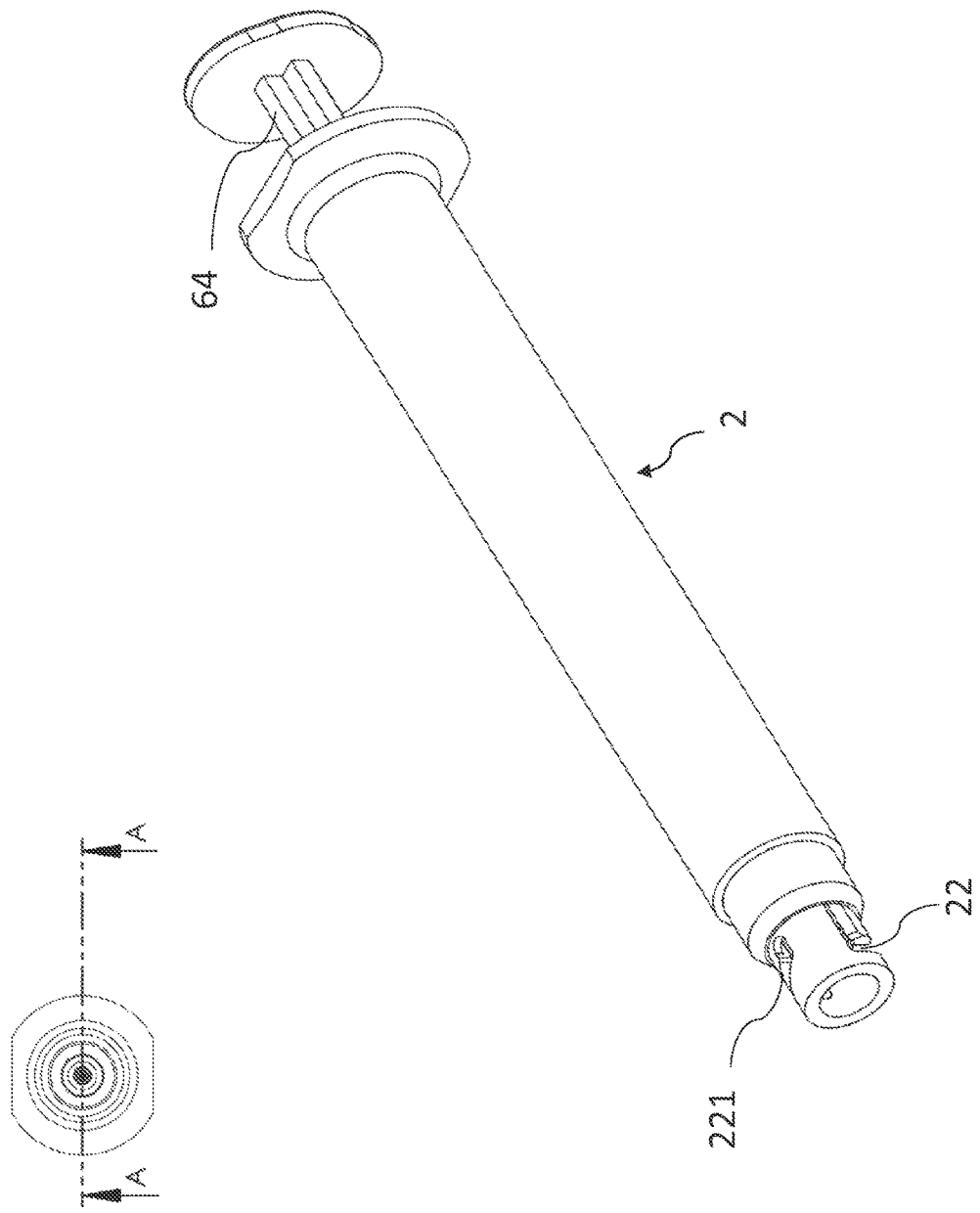
FIG. 3A is a perspective view of a retractable safety syringe and a collapsible plunger thereof in according to a first embodiment of the invention showing that both the needle hub and the collapsible plunger are inserted into the hollow barrel.
Figure 3B:
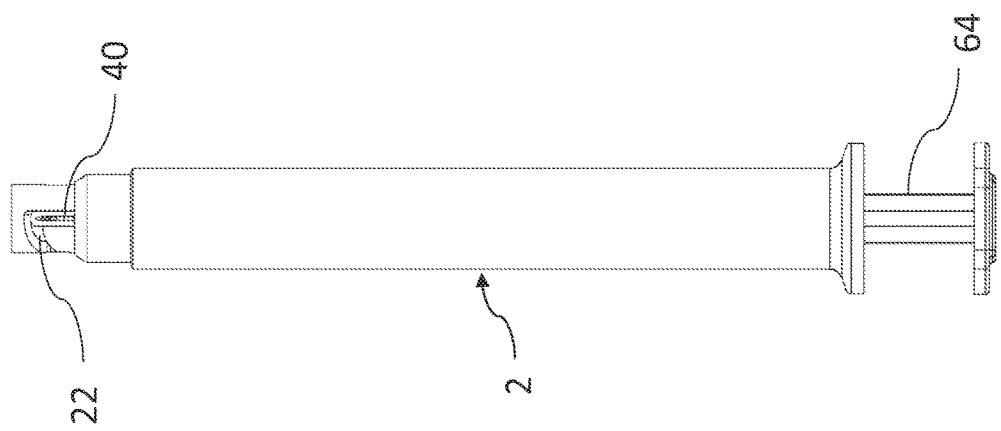
FIG. 3B is a side view of the retractable safety syringe and the collapsible plunger thereof according to the first embodiment of the invention showing that both the needle hub and the collapsible plunger are inserted into the hollow barrel.

Referring to FIGS. 3A and 3B, a perspective view and a side view of a retractable safety syringe 1 and a collapsible plunger 6 thereof according to a first embodiment of the invention are respectively shown, demonstrating that the needle 40 and the collapsible plunger 6 are both inserted into the hollow barrel 2 after the completion of the retraction.

Referring to FIG. 4A to FIG. 4E, a retractable safety syringe 2 according to a second embodiment of the present invention is shown. The retractable safety syringe 2 has all aforementioned features and advantageous designs of the retractable safety syringe 1 according to the first embodiment. In brief, the retractable safety syringe 2 includes: a retractable needle hub 4 having a protrusion 42 (shown in FIG. 4B) formed on an external sidewall 44 of the needle hub 4; a hollow barrel 2 (shown in FIG. 4C) having a curved track 22 (shown in FIG. 4C) formed nearby on a side wall of the hollow barrel 2; a spring 8 (shown in FIG. 4C) is interposed between the external sidewall 44 of the needle hub 4 and the internal sidewall of the hollow barrel 2; and a collapsible plunger 6 consists of a plunger rod 64 and a plunger sleeve 62 (shown in FIG. 4C), wherein the plunger rod 64 is partially telescoped into the plunger sleeve 62 and is releasably interlocked with the plunger sleeve 62, wherein the plunger rod 64 is formed with a protrusion and the plunger sleeve 62 is formed with a longitudinal slot. Therefore, the retraction mechanism of the second embodiment is substantially the same with that of previously described the retractable medical safety syringe 1.

Figure 4A:
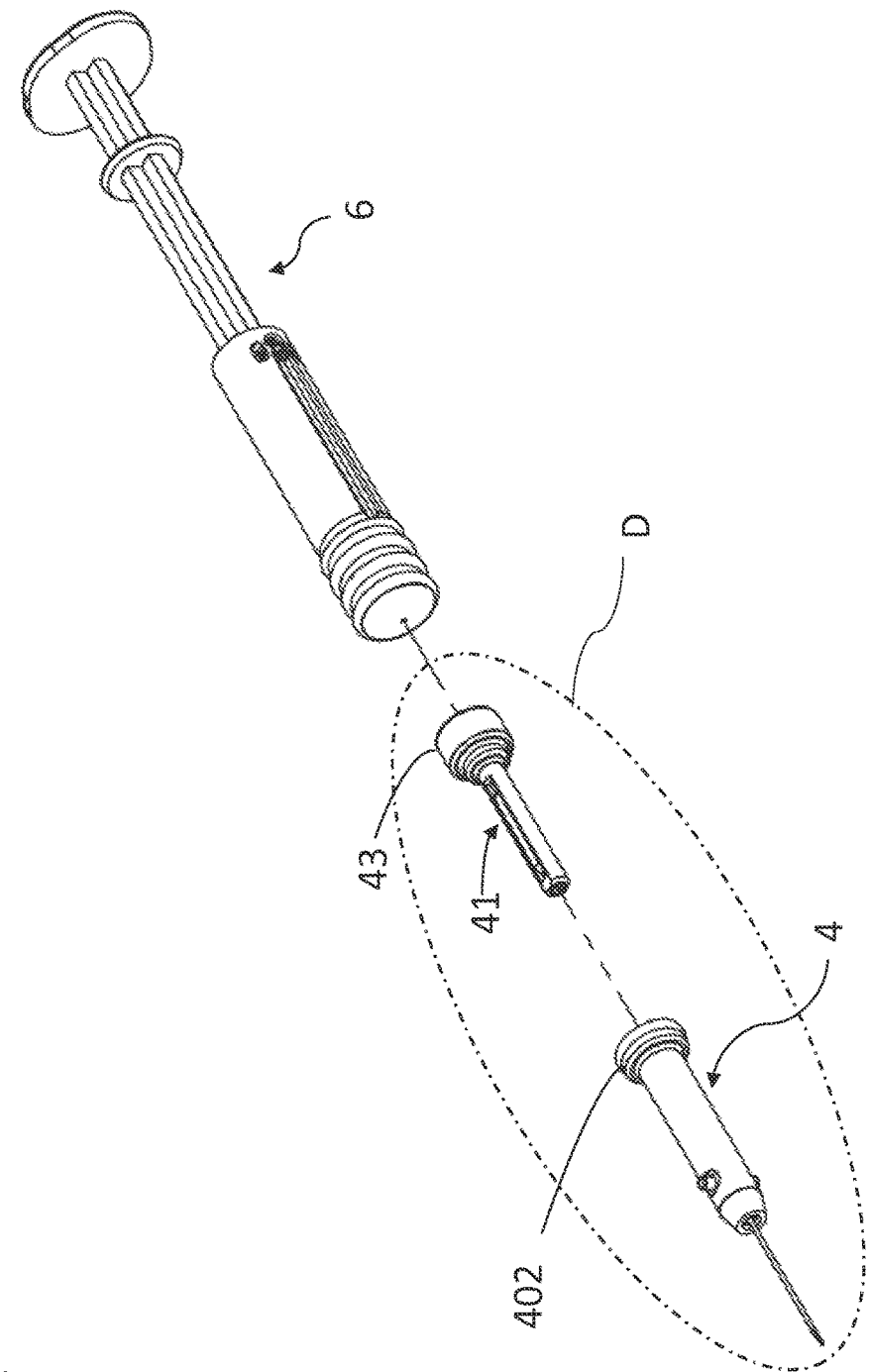
FIG. 4A is an exploded perspective view of the retractable safety syringe and the collapsible plunger thereof according to the second embodiment of the invention.
Figure 4B:
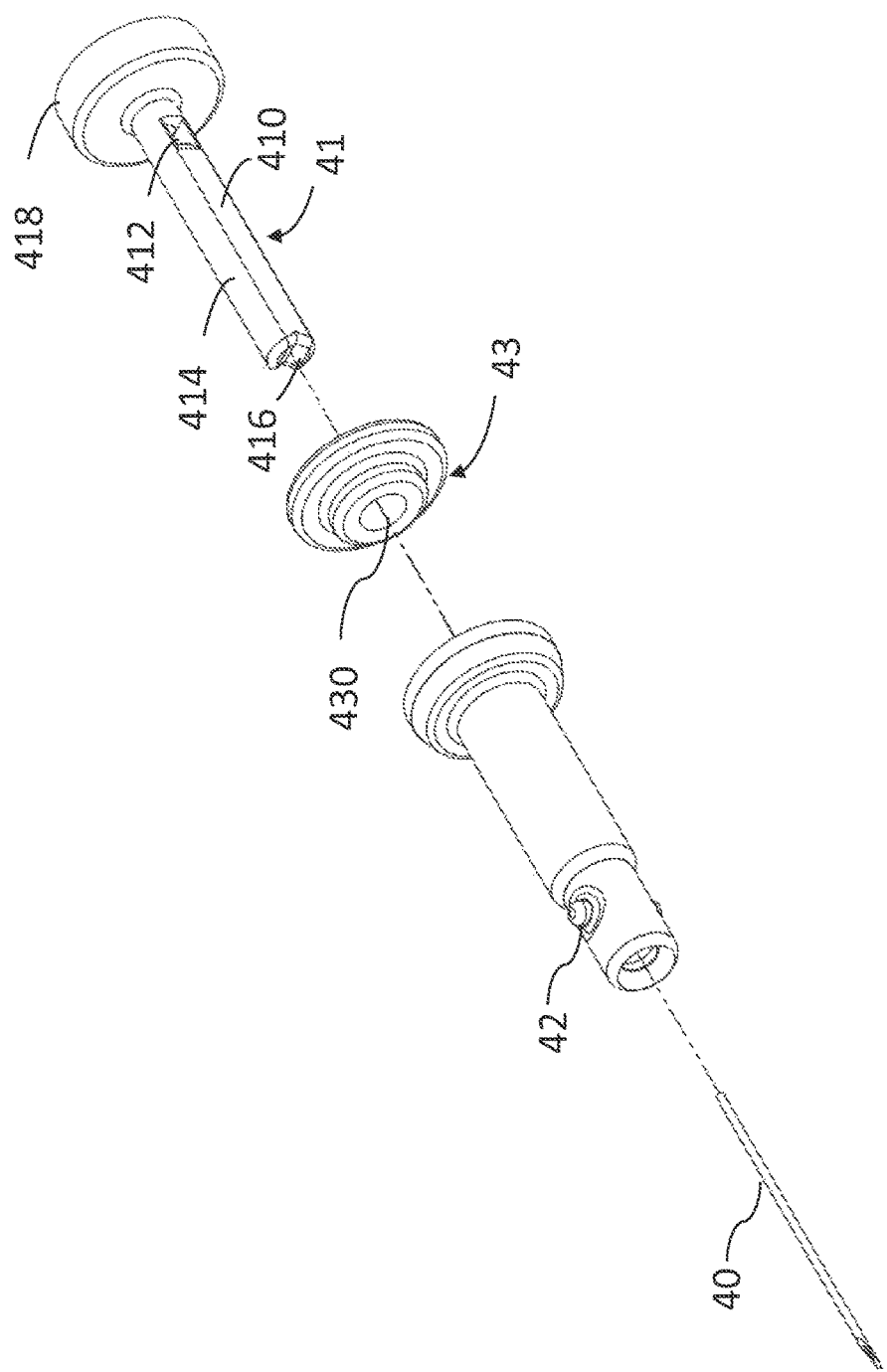
FIG. 4B is an enlarged view of Section D of the retractable safety syringe and the collapsible plunger thereof according to the second embodiment of the invention shown in FIG. 4A.
Figure 4C:
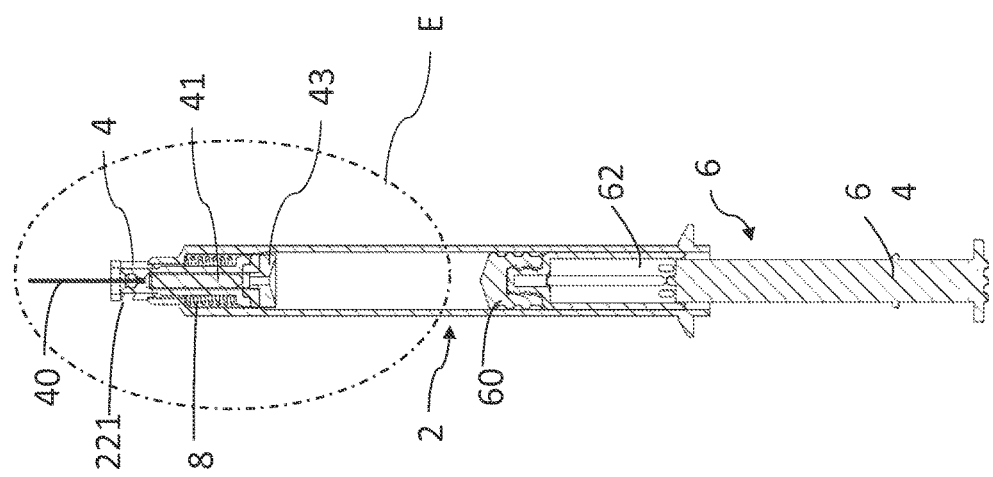
FIG. 4C is a cross-sectional view of the retractable safety syringe and the collapsible plunger thereof showing that the needle hub and the collapsible plunger are not yet inserted into the hollow barrel according to the second embodiment of the invention.

In addition, FIG. 4A to 4E respectively discloses a preferable mode according to the second embodiment of the present invention. As shown in FIGS. 4A and 4B, the retractable needle hub 4 of the retractable safety syringe 2 further has a lumen inside of the needle hub 4 for receiving a plug 41 from the opening of the proximal end 402 of the needle hub 4, the plug 41 includes an elongated cylinder protruding into the lumen of the needle hub 4 and a disc 418 of larger diameter near the proximal end of the plug 41 and has at least one flow path for fluid communication between the lumen of the needle 40 and the fluid chamber inside the hollow barrel 2. It is noted that sufficient space is provided between the internal sidewall of the needle hub 4 (i.e., the sidewall of the needle hub 4 facing the lumen) and the external sidewall of the plug 41 (i.e., the sidewall of the plug 41 facing the lumen), and the space is provided sufficiently for the flow path of the medical materials or the fluid for injection.

Furthermore, a sealing element 43 is further provided for performing the preferable mode of the retractable safety syringe 2. The materials for sealing element 43 is preferable to be but not limited to an elastomeric material with certain hardness such as rubber, thermoplastic elastomer or other macromolecular materials, and thus is suitable for sealing service to prevent the liquid leaking from the jointed seam. For example, an O-ring with desired shape is preferable. Specifically, the sealing element 43 is positioned between the proximal end 402 of the needle hub 4 and the disc 418 of the plug 41. And the sealing element 43 is designed and shaped for being adapted to the proximal end 402 of the needle hub 4 and the disc 418 near the proximal end of the plug, and thus functions to seal the seam between the needle hub 4 and the plug 41.

The sealing element 43 further includes a through-hole 430 in the center of the sealing element 43 which allows the elongated cylinder portion of the plug 41 to pass through the through-hole 430 and enter the lumen of the needle hub 4 at the same time, and then the plug 41 is finally assembled with the needle hub 4 with the sealing element 43 positioned therebetween. Thus, when the elongated cylinder portion of the plug 41 passes through the through-hole 430 and enters the lumen of the needle hub 4 for an desired depth, the disc 418 of the plug 41 adheres the sealing element 43, and thereby the plug 41 itself and the sealing element 43 are secured against the proximal end 402 of the needle hub 4.

Figure 4D:
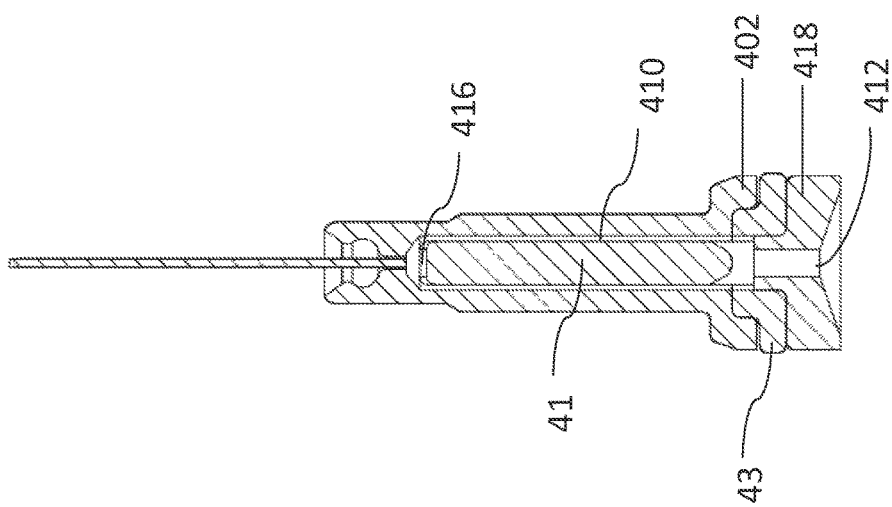
FIG. 4D is an enlarged view of Section E of the retractable safety syringe and the collapsible plunger thereof according to the second embodiment of the invention shown in FIG. 4C.
Figure 4E:
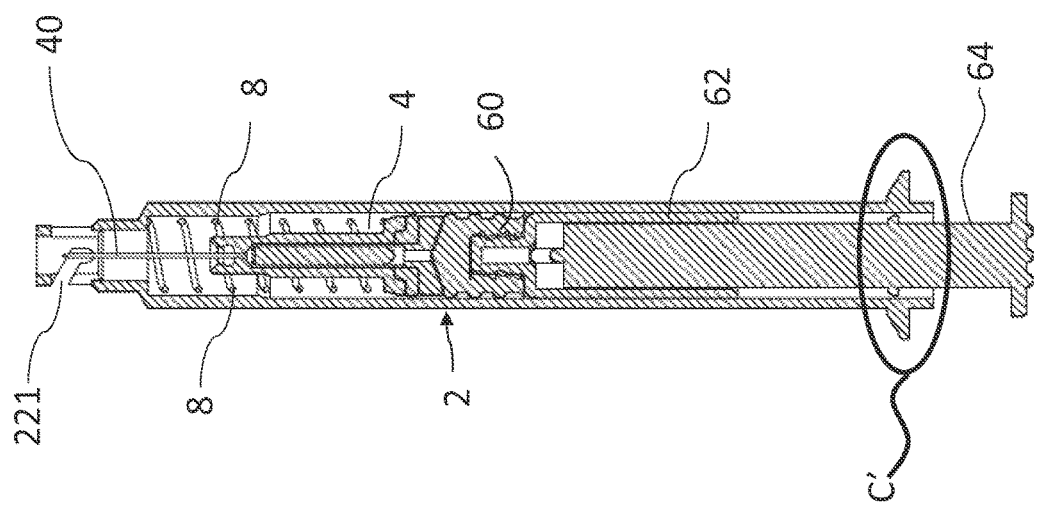
FIG. 4E is a cross-sectional view of the retractable safety syringe and the collapsible plunger thereof according to the second embodiment of the invention showing that both the needle hub and the collapsible plunger are inserted into the hollow barrel.

Referring to FIGS. 4D and 4E, the aforementioned plug 41 is further formed with at least one fluid path 410. Preferably, according to the second embodiment of the present invention, two fluid paths 410 are provided. The fluid paths 410 are provided with an inlet 412 and an outlet 416, which enable the medical materials or fluid of injection (hereinafter "injectant") to flow along the fluid paths 410. More particularly, when the user performs an injection, the injectant flows toward the distal end 201 of the hollow barrel 2, and the injectant flows through the central opening of the disc 418 of the plug 41, the inlet 412, the fluid path 410, and then the outlet 416, and finally arrives at the opening of the distal end 401 of the needle hub 4, followed by the completion of the injection. Alternatively, internal channel disposed inside the plug 41 which extends longitudinally throughout the plug can achieve the similar advantageous effects. Therefore, according to the preferred mode of the second embodiment of the present invention, the dead space inside the needle hub 4 is significantly reduced, which results in less residual and thus less waste of the injectant. Overall, the efficiency and cost of an injection are improved.

Figure 3C:
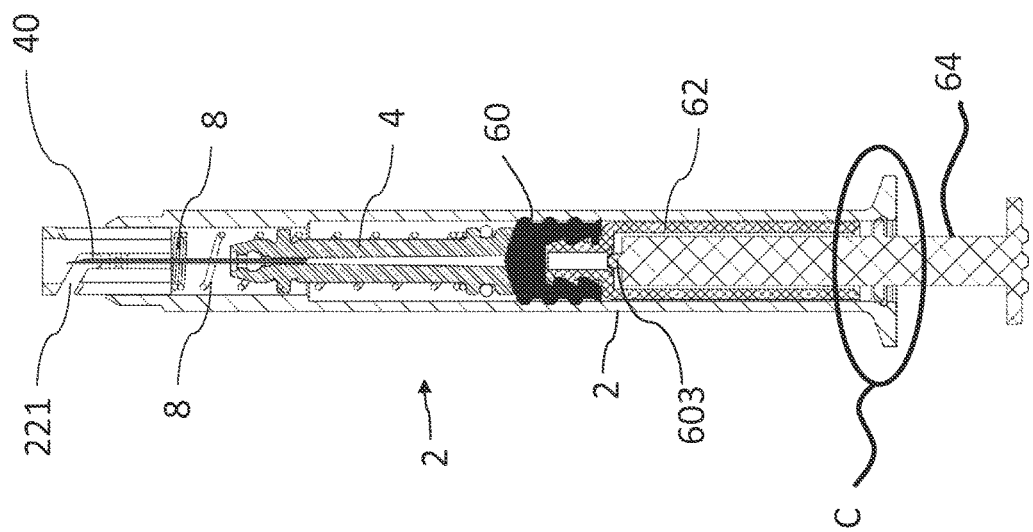
FIG. 3C is a cross-sectional view of the retractable safety syringe and the collapsible plunger thereof according to the first embodiment of the invention showing that both the retractable needle hub and the collapsible plunger are inserted into the hollow barrel.

Further referring to FIG. 5 showing an enlarged view of a section C of the retractable safety syringe 1 and the collapsible plunger 6 thereof according to the first embodiment of the invention shown in FIG. 3C; and the design of section C' of the retractable safety syringe 2 according to the second embodiment of the invention shown in FIG. 4E is substantially same with that of section C of the retractable safety syringe 1. To overcome issues concerning the problems arisen from reusing syringes, a locking means is further provided in this invention. It is noted that the plunger rod 64 is further formed with a raised portion 641 near its proximal end, and the hollow barrel 2 is formed with an annular recessed portion 222 and an adjacent annular raised portion 223 inside the flange 203 of the hollow barrel 2. The raised portion 641 is received and snap-locked by the annular recessed portion 222 and constrained by the annular raised portion 223 when the plunger rod 64 is fully pressed into the hollow barrel 2, render the plunger rod 64 not detachable from the hollow barrel 2 and thus prevent the syringe from being reused. More preferably, the outward appearance of the edge of the raised portion 641 is configured to be have an inclined edge for having better engagement with the annular recessed portion 222, thus the raised portion 641 is firmly constrained by the annular recessed portion 222. And a preferable mode can correspondently made by modifying the configuration of the annular recessed portion 222 to enhance the aforesaid constraint. Therefore, any attempt to pull the plunger rod 64 out of the hollow barrel 2 may impair the retractable safety syringe 1, 2, and thus further reduce the possibility of reusing the retractable safety syringe 1, 2.

Retractable safety syringes, retractable needle hubs, and collapsible plungers are therefore disclosed, whereby the collapsible plunger acts as an actuating means to initiate the retraction mechanism of the needle hub. After an injection is completed, the stopper connecting to the distal end of the collapsible plunger shall be positioned against the proximal end of the needle hub. Upon pressing the collapsible plunger, the retractable needle hub is moved forward along the curved track to the foremost position and stop there and being ready for retraction, an increased force uncouples the collapsible plunger and activates the retraction mechanism simultaneously. Therefore, needle retraction is facilitated by a biasing means, such as a compressed spring or other compressible and de-compressible device.

Typically, the retractable safety syringe is a prefillable syringe which can be prefilled with desired medical materials suitable for injectable combination products. Prior arts of retractable safety syringes requires either an engagement device to couple the stopper or the plunger with the needle holder to enable the needle retractable, or requires a device to disengage the spring retainer so as to decompress the spring accordingly, these complicated configurations often render the fluid chamber vulnerable to compromise the container closure integrity, and thus not suitable for service as prefilled syringes. The disclosed invention hitherto has solved aforementioned shortcomings by providing a more reliable approach for the retraction, and thus improved the container closure integrity of retractable safety syringes by the embodiment of present inventions.

Since such a retractable safety syringe can be made into a ready-to-use product format, the advantages are not limited to enhanced convenience and efficiency of administration by eliminating the drug filling operation, other advantages derived from the aforementioned features, including improved accuracy of dosage, reduced risks of people from exposure to the needlestick injury and incurred infection.

The above embodiments are provided only to demonstrate principles and functions of the present invention and not intended to limit the scope of the present invention. Various changes in form and details may be made by those of ordinary skill in the art without departing from the spirit and scope of the present invention as defined by the following claims.

What is claimed is:

1. A retractable needle assembly of a retractable safety syringe, comprising:
    a needle hub having a first end to receive and hold a needle extending distally, a nearby first guiding means on an side wall of the needle hub, and a second end being opposite to the first end;
    a lumen at the second end of the needle hub for receiving a plug having an elongated cylinder portion protruding into the lumen and a disc portion, and formed with at least one fluid path for communication between the needle and a chamber, wherein the at least one fluid path is an internal channel extending longitudinally throughout the plug and is composed of a plurality of longitudinal recesses alongside an external surface of the elongated cylinder portion of the plug; and
    a hollow barrel having an internal surface defining the chamber allowing the needle hub releasably disposed in the chamber of the hollow barrel, a distal open end allowing the first end of the needle hub to protrude distally, and having a second guiding means nearby on a sidewall of the hollow barrel, and a proximal open end being opposite to the distal open end;
    wherein the second guiding means of the hollow barrel has a first portion and a second portion; and the first guiding means of the needle hub releasably engages with the first portion of the second guiding means, so that the first and the second guiding means are capable of releasably holding the needle hub until the first guiding means disengages from the first portion of the second guiding means and moves toward the second portion of the second guiding means.

2. The retractable needle assembly of claim 1, wherein the first guiding means is a protrusion and the second guiding means is a curved track formed on the internal surface of the hollow barrel and configured to receive the protrusion.

3. The retractable needle assembly of claim 2, wherein the second guiding means extends along a direction being at an angle from 45 degrees to 75 degrees measured from a horizontal plane defined when the whole retractable safety syringe is situated vertically with the needle orientated upward.

4. The retractable needle assembly of claim 3, wherein the angle is 60 degrees measured from the horizontal plane.

5. The retractable needle assembly of claim 1, wherein a sealing element is further provided and shaped for being adapted to the needle hub; and the sealing element is disposed between the second end of the needle hub and the disc portion of the plug.

6. A retractable safety syringe comprising:
    a needle hub having the first end to receive and hold a needle extending distally, a nearby first guiding means on an external wall of the needle hub, and a second end being opposite to the first end;
    a lumen at the second end of the needle hub for receiving a plug having an elongated cylinder portion protruding into the lumen and a disc portion, and formed with at least one fluid path for communication between the needle and a chamber, wherein the at least one fluid path is an internal channel extending longitudinally throughout the plug and is composed of a plurality of longitudinal recesses alongside an external surface of the elongated cylinder portion of the plug; and
    a hollow barrel having an internal surface defining the chamber allowing the needle hub releasably disposed in the chamber of the hollow barrel, a distal open end allowing the first end of the needle hub to protrude distally, and having a second guiding means nearby on a sidewall of the hollow barrel, and a proximal open end being opposite to the distal open end;

a collapsible plunger slideably fitted into the hollow barrel, having a first plunger element having a proximal end and a distal end, a second plunger element being releasably coupled with the first plunger element, wherein the first plunger element is formed with a protrusion near the distal end of the first plunger element, and the second plunger element has a longitudinal slot on a sidewall of the second plunger element to accommodate the protrusion of the first plunger element allowing the protrusion to slide longitudinally along the longitudinal slot, and the longitudinal slot has a proximal part formed with a pinched zone to curb the protrusion and a distal part, so that the first and the second plunger elements are coupled until the pinched zone deforms to disengage the protrusion from the pinched zone, allowing the protrusion sliding toward the distal part of the longitudinal slot, so that the first and the second plunger elements become axially slideable with respect to each other; and a spring disposed between the needle hub and the internal surface of the hollow barrel such that the spring acts between the needle hub and the hollow barrel;

wherein the needle hub is further foinied with at least one fluid path extending longitudinally through the needle, to be in fluid communication with the chamber; and wherein the first guiding means releasably engages with a first portion of the second guiding means, so that the first and the second guiding means are capable of releasably holding the needle hub against an expansion force of the spring until the first guiding means disengage from the first portion of the second guiding means and moves toward a second part of the second guiding means to initiate retraction of the needle hub.

7. The retractable safety syringe of claim 6, wherein the first guiding means is a protrusion and the second guiding means is a curved track formed on the internal surface of the hollow barrel and configured to receive the protrusion.

8. The retractable safety syringe of claim 7, wherein the second guiding means extends along a direction being at an angle from 45 degrees to 75 degrees measured from a horizontal plane defined when the whole retractable syringe is situated vertically with the needle orientated upward.

9. The retractable safety syringe of claim 8, wherein the angle is 60 degrees measured from the horizontal plane.

10. The retractable safety syringe of claim 6, wherein the collapsible plunger is capable of enduring a force less than 98N, so that in normal use the first and the second plunger elements will not be uncoupled.

11. The retractable safety syringe of claim 6, wherein the first plunger element is a rod.

12. The retractable safety syringe of claim 6, wherein the first plunger element is a cylinder.

13. The retractable safety syringe of claim 6, wherein the second plunger element is a sleeve.

14. The retractable safety syringe of claim 6, wherein the second plunger element is a hollow cylinder.

15. The retractable safety syringe of claim 6, wherein the second plunger element further has a plurality of apertures being adjacent to the pinched zone.

16. The retractable safety syringe of claim 6, wherein the first plunger element is provided with a locking means having one or one more annular raised portions near the proximal end, the one or one more annular raised portions being received and snap-locked by an annular recessed portion and an adjacent annular raised portion inside the flange of the hollow barrel, such that the first plunger element is constrained with the hollow barrel by the locking means when the first plunger element is fully pressed into the hollow barrel.

17. The retractable safety syringe of claim 6, wherein a sealing element is further provided and shaped for being adapted to the needle hub and the sealing element is disposed between the second end of the needle hub and the disc portion of the plug.

* * * * *